US010035982B2

(12) United States Patent
Rouy et al.

(10) Patent No.: US 10,035,982 B2
(45) Date of Patent: *Jul. 31, 2018

(54) METHOD OF PREPARING AUTOLOGOUS CELLS AND METHODS OF USE FOR THERAPY

(71) Applicant: BioCardia, Inc., San Carlos, CA (US)

(72) Inventors: Didier Rouy, San Carlos, CA (US); Peter A. Atlman, Menlo Park, CA (US); Benjamin Koziner, Buenos Aires (AR)

(73) Assignee: BioCardia, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/664,988

(22) Filed: Jul. 31, 2017

(65) Prior Publication Data

US 2017/0327790 A1   Nov. 16, 2017

Related U.S. Application Data

(63) Continuation of application No. 15/055,418, filed on Feb. 26, 2016, now Pat. No. 9,752,123, which is a continuation of application No. 12/434,537, filed on May 1, 2009, now Pat. No. 9,301,975.

(51) Int. Cl.
| | |
|---|---|
| *C12N 5/00* | (2006.01) |
| *C12N 5/0775* | (2010.01) |
| *A61K 35/28* | (2015.01) |
| *A61K 9/00* | (2006.01) |
| *A61K 35/10* | (2015.01) |
| *A61K 35/00* | (2006.01) |
| *C12Q 1/6883* | (2018.01) |
| *A61K 35/12* | (2015.01) |

(52) U.S. Cl.
CPC .......... *C12N 5/0663* (2013.01); *A61K 9/0019* (2013.01); *A61K 35/00* (2013.01); *A61K 35/10* (2013.01); *A61K 35/28* (2013.01); *A61K 2035/124* (2013.01); *C12N 2500/84* (2013.01); *C12N 2502/11* (2013.01); *C12Q 1/6883* (2013.01); *C12Q 2600/106* (2013.01); *C12Q 2600/156* (2013.01); *C12Q 2600/158* (2013.01)

(58) Field of Classification Search
CPC .............................. C12N 5/0663; A61K 35/28
See application file for complete search history.

(56) References Cited

U.S. PATENT DOCUMENTS

| | | |
|---|---|---|
| 6,261,549 B1 | 7/2001 | Fernández et al. |
| 6,281,012 B1 | 8/2001 | McIntosh et al. |
| 6,322,784 B1 | 11/2001 | Pittenger et al. |
| 6,328,960 B1 | 12/2001 | McIntosh et al. |
| 6,342,370 B1 | 1/2002 | Connolly et al. |
| 6,355,239 B1 | 3/2002 | Bruder et al. |
| 6,358,702 B1 | 3/2002 | Connolly |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,541,024 B1 | 4/2003 | Kadiyala et al. |
| 6,685,936 B2 | 2/2004 | McIntosh et al. |
| 6,709,864 B1 | 3/2004 | Pittenger et al. |
| 6,761,887 B1 | 7/2004 | Kavalkovich et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 7,029,666 B2 | 4/2006 | Bruder et al. |
| 7,101,704 B1 | 9/2006 | Mosca |
| 8,496,926 B2 | 7/2013 | De La Fuente et al. |
| 9,301,975 B2 | 4/2016 | Rouy et al. |
| 9,752,123 B2 | 9/2017 | Rouy et al. |
| 2005/0112104 A1 | 5/2005 | Pittenger et al. |
| 2005/0265980 A1 | 12/2005 | Chen et al. |
| 2006/0003365 A1 | 1/2006 | Shaughnessy et al. |
| 2007/0037144 A1 | 2/2007 | Wohlgemuth et al. |

(Continued)

FOREIGN PATENT DOCUMENTS

| | | |
|---|---|---|
| WO | WO-9957130 A1 | 11/1999 |
| WO | WO-2008023566 A1 | 2/2008 |

(Continued)

OTHER PUBLICATIONS

Chen et al. Am. J. Cardiol. 94:92-95. (Year: 2004).*
Zappia et al. Blood106:1755-1761. (Year: 2005).*
da Silva, et al. Methodology, biology and clinical applications of mesenchymal stem cells. Frontiers in Bioscience, 14:4281-4298, 2009.
Deng, et al. Noninvasive discrimination of rejection in cardiac allograft recipients using gene expression profiling. Am J Transplant. Jan. 2006;6(1):150-60.
European search report and written opinion dated Feb. 1, 2011 for EP Application No. 10770479.3.

(Continued)

*Primary Examiner* — Marcia S Noble
(74) *Attorney, Agent, or Firm* — Wilson Sonsini Goodrich & Rosati

(57) ABSTRACT

A method for expanding mesenchymal cells derived from autologous bone marrow in autologous culture medium which can be used in a clinical setting, and a business method for performing such expansions in the future as a service for patients. A method for expanding mesenchymal cells derived from autologous bone marrow in autologous culture medium including a diagnostic kit for the autologous cell therapy to determine whether a patient will respond to the autologous cell therapy for treatment of a disease, in which said kit comprising a system for detecting gene and protein expression comprising at least two isolated DNA molecules wherein each isolated DNA molecule detects expression of a gene that is differentially expressed in the tissue of the patient that is intended to be the source of the autologous cell therapy.

7 Claims, 4 Drawing Sheets

(56) References Cited

U.S. PATENT DOCUMENTS

| | | |
|---|---|---|
| 2008/0111272 A1 | 5/2008 | Burgess et al. |
| 2009/0035286 A1 | 2/2009 | Minguell et al. |
| 2010/0166712 A1 | 7/2010 | Sadiq et al. |
| 2016/0228469 A1 | 8/2016 | Rouy et al. |

FOREIGN PATENT DOCUMENTS

| | | |
|---|---|---|
| WO | WO-2009033162 A1 | 3/2009 |
| WO | WO-2010127342 A2 | 11/2010 |

OTHER PUBLICATIONS

Garcia-Olmo et al., Dis Colon Rectum 48(7) :1416-1423, 2005. Abstract only.
Hattan, et al. Purified cardiomyocytes from bone marrow mesenchymal stem cells produce stable intracardiac grafts in mice. Cardiovascular Research, Oxford University Press, GB, vol. 65, No. 2, Feb. 1, 2005, pp. 334-344.
International search report and written opinion dated Feb. 1, 2011 for PCT/US2010/033378.
Leri, et al. Myocardial regeneration and stem cell repair. Current Problems in Cardiology, Year Book Medical Publishers, Chicago, US, vol. 33, No. 3, Jan. 31, 2008, pp. 91-153.
Li et al. Original Research Report. Morphological transformation in esophageal submucosa by bone marrow cells: Esophageal implantation under external esophageal perfusion. Stem Cell and Development. 15:697-705, 2006.
Ming Zhang, et al. SDF-1 expression by mesenchymal stem cells results in trophic support of cardiac myoctyes after myocardial infarction. Faseb Journal, Fed. of American Soc. for Experimental Biology, US, vol. 21, No. 12, Oct. 1, 2007, pp. 3197-3207.
Notice of allowance dated Apr. 27, 2017 for U.S. Appl. No. 15/055,418.
Notice of allowance dated May 9, 2017 for U.S. Appl. No. 15/055,418.
Notice of allowance dated Dec. 21, 2015 for U.S. Appl. No. 12/434,537.
Office Action dated May 13, 2015 for U.S. Appl. No. 12/434,537.
Office action dated Jul. 22, 2016 for U.S. Appl. No. 15/055,418.
Office Action dated Dec. 23, 2014 for U.S. Appl. No. 12/434,537.
Office Action dated Mar. 22, 2012 for U.S. Appl. No. 12/434,537.
Office Action dated Jul. 12, 2011 for U.S. Appl. No. 12/434,537.
Office Action dated Jul. 17, 2014 for U.S. Appl. No. 12/434,537.
Segers, et al. Stem-cell therapy for cardiac disease. Nature, vol. 451, Feb. 21, 2008, pp. 937-942.
Strauer, et al. Renegeration of human infarcted heart muscle by intracoronary autologous bone marrow cell transplantation in chronic coronary artery disease. J Am Coll Cariol 46: 1651-58, 2005.
Vandervelde, et al. Stem cell-related cardiac gene expression early after murine myocardial infarction. Cardiovasc. Res., vol. 73, No. 4, pp. 783-793, Mar. 1, 2007—See figures 3-5; Abstract.
Zappia, et al. Mesenchymal stem cells ameliorate experimental autoimmune encephalomyelitis inducing T-cell anergy. Blood 106(5):1755-1761, 2005.

* cited by examiner

Fig. 4

|  |  | CD13 | CD105 | CD90 | CD14 | CD45 | CD44 | CD34 | CD61 | CD73 |
|---|---|---|---|---|---|---|---|---|---|---|
| Patient 1 | FCS | 98.5 | 96.2 | 99.4 | 0.3 | 0.7 | 98.1 | 0.1 | 0.4 | 97.8 |
|  | AS | ND | 73.8 | 74.6 | 26.5 | 24.4 | ND | ND | ND | 61.2 |
|  | F&T PRP | 99.3 | 99.5 | 99.6 | 1.3 | 1 | 99.2 | 0.1 | 0.3 | 89.2 |
|  | tPRP | ND | 96.5 | 94.7 | 4.7 | 0.4 | 78.2 | 0.2 | 0.3 | 99.5 |
| Patient 2 | FCS | 99.4 | 99.4 | 99.1 | 0.9 | 1.8 | 99.2 | 0.8 | 0.3 | 99.3 |
|  | AS | 99 | 99 | 99.3 | 0.6 | 4.1 | 96.8 | 1.2 | 1.9 | 99.5 |
|  | F&T PRP | 99.7 | 99.6 | 99.1 | 0.2 | 3.3 | 93.8 | 0.1 | 2.1 | 99.7 |
|  | tPRP | 99.8 | 99.4 | 99.7 | 0.7 | 5.5 | 98.4 | 0.1 | 2.4 | 99.6 |
| Patient 3 | FCS | 99.0 | 99.5 | 99.4 | 0.5 | 4.5 | 98.4 | 0.6 | 0.1 | 99.4 |
|  | AS | 97.1 | 98.0 | 98.1 | 3.5 | 7.1 | 98.1 | 1.2 | 0.2 | 95.6 |
|  | F&T PRP | 98.9 | 98.4 | 99.1 | 0.8 | 6.2 | 95.4 | 0.4 | 2.2 | 97.1 |
|  | tPRP | 98.7 | 98.9 | 99.4 | 2.0 | 2.0 | 99.4 | 1.5 | 0.6 | 98.2 |
| Patient 4 | FCS | 97.9 | 97.5 | 97.7 | 2.8 | 6.6 | 95.4 | 2.1 | 2.4 | 84.6 |
|  | AS | 98.2 | 98.4 | 97.2 | 6.4 | 5.3 | 98.9 | 0.7 | 3.9 | 95.8 |
|  | F&T PRP | 99.6 | 98.9 | 99.4 | 1.0 | 4.0 | 96.2 | 0.1 | 0.7 | 99.0 |
|  | tPRP | 98.1 | 99.5 | 98.4 | 2.2 | 0.8 | 97.5 | 0.2 | 0.3 | 97.2 |
| Expected in | MSCs | 100 | 100 * | 100 * | 0 * | 0 * | 100 | 0 | 0 | 100 * |
| Known in: |  | stem mono Mac Epi endo | Stem Endoth | Stem Endoth | Mono Mac Granulo | Lympho stem Mono/mac Granulo | All | Stem Endot | Mono/mac Plate Endoth | Lympho Stem Endoth Epit |

METHOD OF PREPARING AUTOLOGOUS CELLS AND METHODS OF USE FOR THERAPY

CROSS-REFERENCE TO RELATED APPLICATIONS

This application is a continuation of U.S. patent application Ser. No. 15/055,418, filed Feb. 26, 2016, now U.S. Pat. No. 9,752,123, which is a continuation of U.S. patent application Ser. No. 12/434,537, filed May 1, 2009, now U.S. Pat. No. 9,301,975, the entire contents of which are incorporated herein by reference.

BACKGROUND OF THE INVENTION

1. Field of the Invention

The inventions described below relate the field of autologous cell therapy.

In our prior U.S. patent application Ser. No. 11/735,869, filed Apr. 16, 2007, we described a treatment for patients suffering from chronic myocardial infarction by injecting autologous bone marrow cells in or near the areas of chronic myocardial infarction in the patient's heart. In addition to the mononuclear cells, mesenchymal cells, CD-34 positive cells, CD-90 positive cells, and CD-133 positive cells mentioned in therein, additional cell therapies may be applicable to other cardiac conditions. Each of these cell therapies may be useful to treat chronic myocardial infarction, acute myocardial infarction, myocardial ischemia, chronic myocardial ischemia, heart failure, cardiovascular disease, and peripheral vascular disease. U.S. patent application Ser. No. 11/735,869, U.S. is hereby incorporated by reference.

Human bone marrow mesenchymal cells (hMSCs) are currently being investigated for a number of clinical applications including cardiovascular repair, orthopaedic repair, connective tissue repair, and immune diseases such as graft versus host disease, Crohn's disease. They have potential roles in other immune diseases such as lupus, osteoarthritis and rheumatoid arthritis as well as well as diabetes. They also have potential to act as carriers of gene-based therapeutics with ex vivo transfection of the cells to enhance the control of gene based therapeutics dosing. The following prior art references are hereby incorporated by reference: U.S. Pat. Nos. 7,101,704; 7,029,666; 6,875,430; 6,863,900; 6,835,377; 6,797,269; 6,761,887; 6,709,864; 6,685,936; 6,541,024; 6,387,369; 6,387,367; 6,379,953; 6,368,636; 6,358,702; 6,355,239; 6,342,370; 6,328,960; 6,322,784; 6,281,012; 6,261,549.

Although it has been argued that allogenic cells have great potential to provide an off the shelf product for patients because they will not be recognized as foreign by the recipient patient, this has not yet been proven. Allogenic cells have a greater propensity (compared to autologous cells) to carry diseases from the donor to the recipient and have a greater propensity for rejection of the therapeutic cells by the immune system of the patient who received them.

Expansion of autologous hMSC in a truly autologous culture medium that contains no animal serum or allogenic culture additives for clinical transplantation to the patient, which has not previously been proposed, should also be valuable avoiding the problems associated with allogenic cells. To date, reported clinical trials are employing human bone marrow mesenchymal stromal cells generated in a culture medium supplemented with fetal calf serum (FCS). FCS is an undesired source of xenogeneic antigens and bears the risk of transmitting animal viral prion and zoonose contaminations. Additionally FCS has been implicated with anaphylactic or arthus like immune reactions in patients who received cells generated in FCS supplemented medium even leading to arrhythmias after cardioplasty (Chachques 2004).

Early work on autologous serum hMSC has recently been shown to be promising by Stute et al 2004, but the amount of autologous serum required is identified as a significant hurdle to clinical expansion such that the investigators proposed using 1% and 3% autologous serum in the culture medium even though they had far superior results at 10% autologous serum. Other investigators have also shown a faster proliferation compared to FCS at least during first passages without loss of the typical phenotype, motility, and differentiation capabilities in vitro, whereas allogenic human serum resulted in hMSC growth arrest and death (Kobayashi et al 2005, Shandahar et al 2005, Mizuno et al 2006).

The primary reason presented that autologous serum cannot be considered as a general substitute for FCS is the amount of autologous serum necessary for sufficient expansion would exceed the amount a donor could provide (Lange et al 2007). Lange et al 2007 proposed the use of pooled platelet lysates to create an activated plasma to avoid the use of FCS, but their solution falls short of that provided here in that they are pooling the platelets from multiple donors to create an allogenic culture medium.

Here we disclose three methods to culture bone marrow or adipose tissue derived autologous culture medium expanded autologous mesenchymal stem cells (ACMEAM's) from the bone marrow or adipose tissue. These inventive methods have enormous value and have been validated in both a swine and human and are comparable to the gold standard of culturing in 10% fetal calf serum.

BRIEF SUMMARY OF THE INVENTION

The methods and devices described below provide for treatment of several cardiovascular diseases with autologous culture medium expanded autologous mesenchymal stem cells (ACMEAM's) from the bone marrow. To treat a patient with the various cardiovascular diseases, including chronic myocardial infarction, myocardial ischemia, acute myocardial infarction, congestive heart failure, atherosclerosis, coronary artery disease, and peripheral artery disease, blood components and a source of MSCs (typically bone marrow or adipose tissue stromal cells) are extracted from the patient. Autologous culture medium is prepared from the blood components and the extracted MSCs are expanded to create ACMEAMs over a period of weeks for subsequent characterization and administration to the patient. The cells are expanded in the autologous culture medium developed from the blood components as described. When sufficient population of expanded cells has been grown, the cells are administered to the patient from whom they were harvested, in or near the site of the disease to be treated.

These therapies are extremely expensive, perhaps $10,000 to $50,000 per therapeutic dose of approximately 20 to 100 million cells delivered in a volume of 1.0 to 5.0 ml which is typically, but not necessarily, used in a single session of tissue injections.

BRIEF DESCRIPTION OF THE DRAWINGS

FIG. 4 is a table of CD Profiles in Human Cultured Autologous Bone Marrow Mononuclear Cells in Fetal Calf Serum (FC), Autologous Serum (AS), Freeze and Thaw Platelet Activated Plasma, (F&T PRP) and Thrombin Activated Platelet Activated Plasma (tPRP).

DETAILED DESCRIPTION OF THE INVENTIONS

Three separate preferred methods for creating autologous culture medium are provided. These involve adding to a base medium one of the following three (1) autologous serum at 10% by volume, (2) activated plasma developed from thaw freeze platelet lysates at 5% by volume, and (3) activated plasma made by thrombin activation at 5% by volume.

(1) ACMEAMs in Autologous Serum

The treatment method starts with harvesting both blood from the patient, and harvesting stem cells from the patient. It has been noted in the literature that the generation of autologous serum for culturing is difficult in that many patients cannot provide sufficient blood to enable expansion of the stem cells from the patient in the serum from the patient. The solution here on the surface will appear quite simple, but it is not the preferred embodiment of this invention as it is far more complex clinically than the other two solutions.

The problem that makes autologous serum not a solution for patient therapeutics is that many patients, particularly those with a significant cardiovascular disease, cannot donate sufficient blood in a single visit to enable successful cell growth. This problem of obtaining enough autologous serum in a single visit to culture cells, is solved by having them donate the tissue for culturing on multiple separate occasions with a sufficient time lag between the blood harvest for them to have regenerated. In this invention, the patient's own serum will be used to avoid fetal calf serum and provide for autologous serum to grow mesenchymal cells taken from bone marrow. To obtain this serum, 250 ml of blood will be taken from each patient at each of two visits separated between one and three weeks apart for a total blood volume of 500 ml of blood. This blood will be stored as a source for autologous tissue culture medium. This type of thinking goes against typical medical practice as one desires to have the patient see the physician as little as possible, and spend as little time as possible within the hospital. Physician and hospital time is expensive. The additional time to generate the autologous serum also slows the delivery of therapy which is also not desirable. Further, having multiple tissue harvest points requires additional control in tracking the blood volumes that will be used to form serum as well as the cell source from which the mesenchymal cells will be expanded. However donating blood products at two or more time points before the therapy does provide a solution to generating autologous serum.

The disadvantage of the delay in cell processing could be addressed by continuing to harvest tissue during the culturing process as the need for autologous serum increases exponentially over time with the expansion of the cultures. Although this is theoretically feasible, it makes no sense from a manufacturing process perspective as many logistic issues could result in a lack of inputs at critical periods during the culture process.

Figure 1:
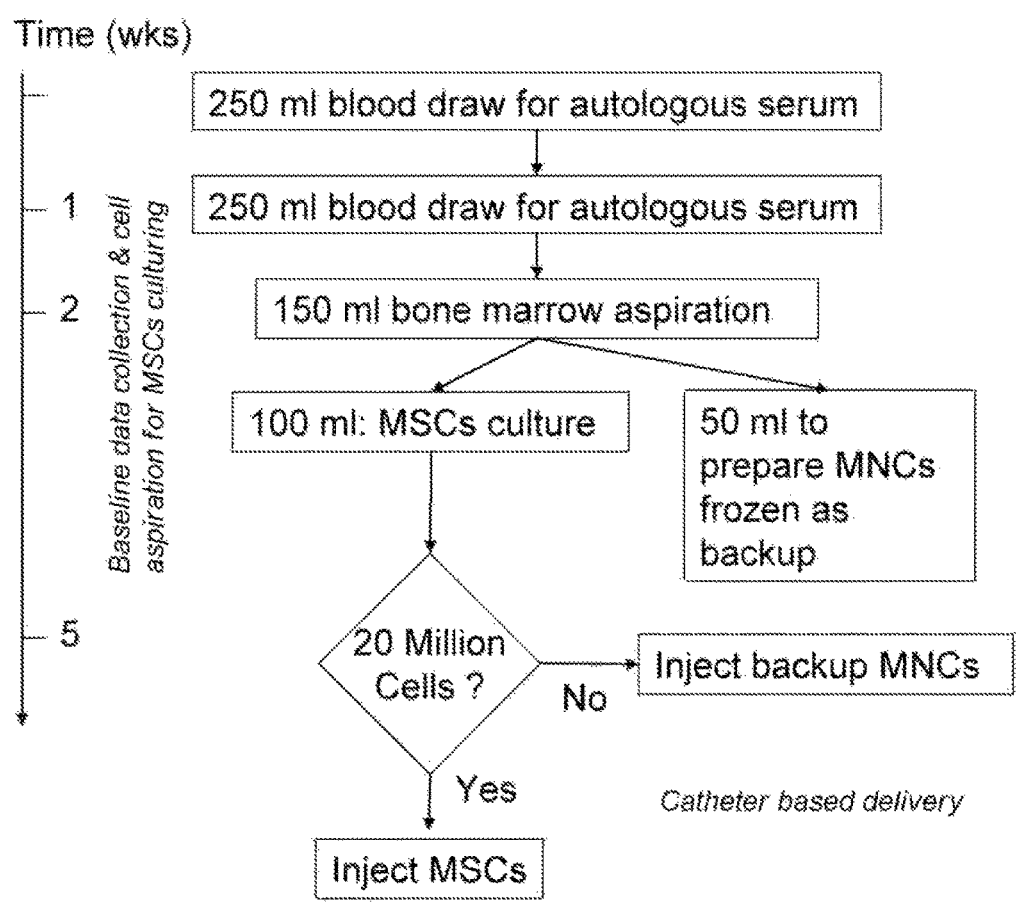
FIG. 1 illustrates a method for preparing autologous culture medium expanded autologous mesenchymal stem cells (ACMEAMs) from the bone marrow.
Figure 2A:
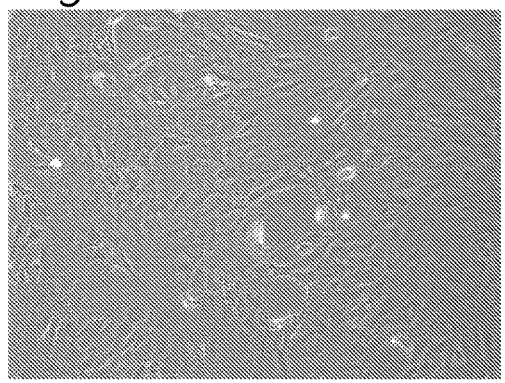
FIGS. 2a through 2d show comparative photographs of Swine mesenchymal stromal stem cells taken from the bone marrow and cultured for 18 days in (FIG. 2a) 10% fetal calf serum, (FIG. 2b) 10% autologous serum, (FIG. 2c) 5% platelet rich plasma where platelets were lysed with a freeze thaw cycle, and (FIG. 2d) 5% platelet rich plasma where platelets were lysed with a thrombin activation.
Figure 2B:
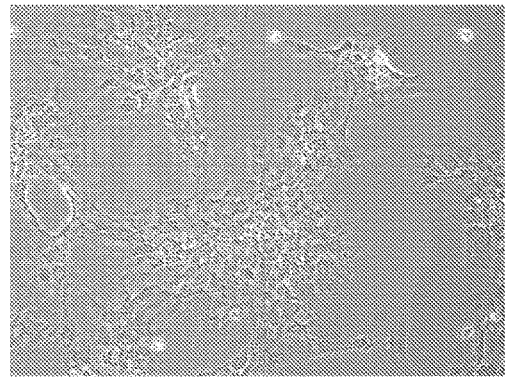
Figure 2C:
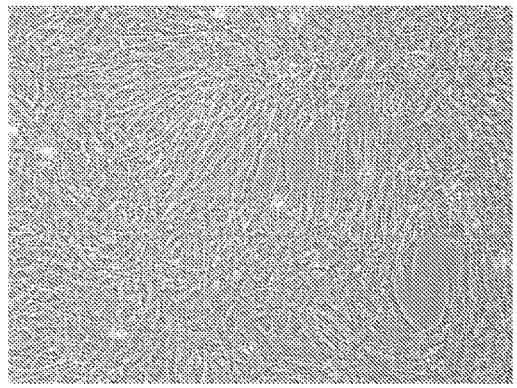
Figure 2D:
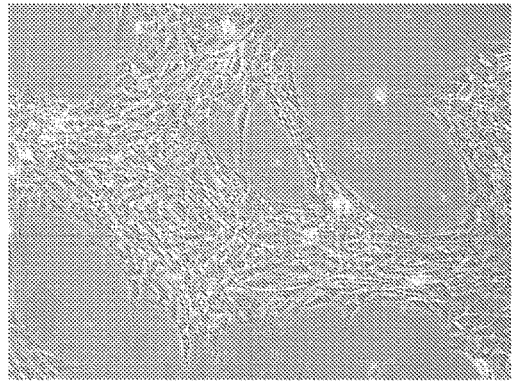
Figure 3A:
FIGS. 3a through 3d show comparative photographs of Human mesenchymal stromal stem cells taken from the bone marrow and cultured for 11 or 13 days in (FIG. 3a) 10% fetal calf serum, (FIG. 3b) 10% autologous serum, (FIG. 3) 5% platelet rich plasma where platelets were lysed with a freeze thaw cycle, and (FIG. 3d) 5% platelet rich plasma where platelets were lysed with a thrombin activation.
Figure 3B:
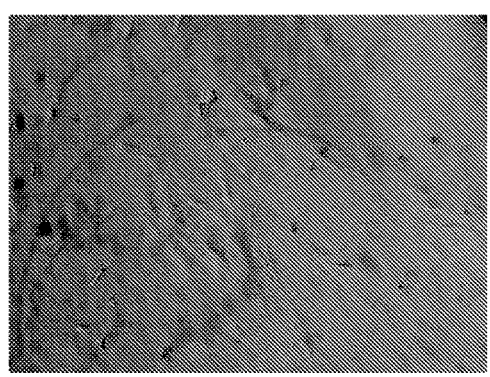
Figure 3C:
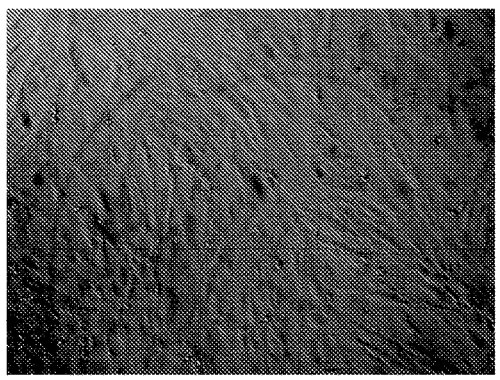
Figure 3D:
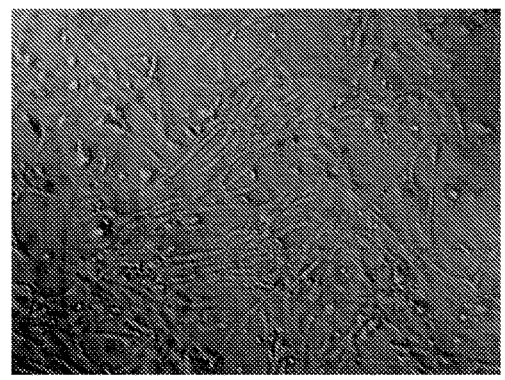

FIG. 1 shows this method and neatly solves the hurdle of both enabling the development of autologous serum to expand ACMEAMs as well as a fall back strategy to deliver a preparation of MNCs should the ACMEAMs not culture as expected. Patients will have up to 150 ml of bone marrow aspirated under local anesthesia. Up to 100 ml will be used to expand the mesenchymal cell population in this autologous serum to develop a dosage of up to 100 million MSCs, with a minimum of 20 million MSCs. Patients who are not eligible for MSCs due to difficulties in culturing a minimum of 20 million MSCs may be eligible to receive frozen MNCs at a dosage of 100 million cells which is the same dosage previously delivered by our group in a clinical setting with good results.

In this invention, 250 ml of blood will be taken from the patient to obtain autologous serum roughly five weeks before therapy is scheduled and an additional 250 cc will be taken roughly four weeks before therapy to provide for 500 cc of blood to provide for autologous serum. Roughly three weeks before therapy (such as cardiac catheterization for delivery in a setting of heart failure) 150 ml of autologous bone marrow mononuclear cells will be aspirated under local anesthesia from the posterior iliac crest. Bone marrow mononuclear cells will be isolated by density gradient on Ficoll-Paque Plus tubes (Amersham Biosciences). Cells will be washed and filtered through 100 .mu.m nylon mesh to remove cell aggregates.

The blood and bone marrow are transported to a laboratory for processing, including separation of the mesenchymal stem cells from the bone marrow, and culturing and expanding a portion of mesenchymal stem cells (while preserving a portion of the mesenchymal stem cells for later use, including re-supply of mesenchymal stem cells should the processed portion fail). The mesenchymal stem cells are expanded until a population of up to 200 million cells is achieved.

Cells are divided into two fractions. One fraction will be cultured in three (3) T225 cm.sup.2 Falcon flasks (Becton Dickinson) providing cells that will then be seeded into thirty (30) T225 cm.sup.2 flasks to generate up to 200 million P1 cells using the autologous serum. Ten percent of the final cell solution will be used for cell counting and viability testing using trypan blue exclusion and bacteriological analysis. A second fraction will be frozen for future use if the number of cultured hMSCs do not reach the acceptable 20 million level. This second fraction may be used in an attempt to deliver MNCs as shown in FIG. 1 or saved to attempt an expansion of the frozen cells at a later date.

The expanded population of up to 20M cells is then frozen and transported to the medical facility where the treatment is to be performed, and cells are thawed, washed, and re-suspended just prior to delivery at a concentration of up to 4.0.times.10^7 cells/ml in a total volume of up to 5 ml.

(2) ACMEAMs in Activated Plasma with Platelet Freeze Thaw

Blood components (serum, plasma, platelets and their derivatives) are obtained through apheresis according to standard procedure. There are numerous types of apheresis. Blood taken from a healthy donor can be separated into its component parts, where the needed component is collected and the "unused" components are returned to the donor. Fluid replacement is usually not needed in these type of collections. There are large categories of component collections: Plasmapheresis—blood plasma. Plasmapheresis is useful in collecting FFP (fresh frozen plasma). Plateletpheresis (thrombapheresis, thrombocytapheresis)—blood platelets. Plateletpheresis, like it sounds, is the collection of platelets by apheresis; while returning the red blood cells, white blood cells, and component plasma. The yield is normally the equivalent of between six and ten random platelet concentrates. Leukapheresis—leukocytes (white blood cells). Leukopheresis is the removal of PMN's, basophils, eosinophils typically for transfusion into patients whose PMN's are ineffective or traditional therapy has failed.

Apparatus such as Haemonetics MCS+9000 or COBE 2991 with sterile single use consumables are used. After the venous access is secured, the speed is set up to 60 ml/min. A maximum of 15% of the total blood volume is sampled according to the standard tables (i.e. a 75 KG patient has a total blood volume of 5250 ml and 787 ml may be sampled). The red cells are infused back. The whole procedure takes 1-2 hours and yields 10.sup.11 to 5.times.10.sup.11 platelets.

The Apheresis produces platelet rich plasma (up to 250 ml) which are split into 50 ml bags using sterile techniques. Bone marrow is processed as before on the same day and sent to the processing lab in the same package with the platelet rich plasma.

At the processing lab, the platelet rich plasma bags are then frozen in liquid nitrogen for 5 seconds and then thawed under 37 .degree. C. water and then frozen again in liquid nitrogen. After the second thaw they are transferred into 15 ml falcon conical tubes and frozen at −20 .degree. C. These tubes are then thawed for the culture medium and added to the culture base medium alpha MEM from GIBCO at 5% to 10% upon which the mononuclear cells containing mesenchymal cells obtained as described previously are plated out similarly as previously described.

The advantage of this approach is that even with a large marrow aspiration of 150 ml, the total volume loss for the patient is only 150 ml. This can be done on volumes of marrow as small as 50 ml. Further, the procedure for quality control just became enormously simpler as the patient presents at the hospital at one time point and the reagents for cell culture are shipped and processed at the lab at one time point. This is enormously valuable.

(3) ACMEAMs in Activated Plasma with Platelet Thrombin Activation

Platelet rich plasma and autologous bone marrow are obtained and shipped to processing lab on the same day as described previously.

At the processing lab, one unit of thrombin per ml is added to the platelet rich plasma bags containing 150 ml. Thrombin activated platelet rich plasma is then gently shaken for 45 minutes at room temperature, followed by transfer into 50 ml conical tubes and spun to eliminate platelet aggregates. Supernatent is aliquoted in 15 ml tubes and frozen for further supplementing the culture medium. These tubes are then thawed for the culture medium and added to the culture base medium alpha MEM from GIBCO at 5% to 10% upon which the mononuclear cells containing mesenchymal cells obtained as described previously are plated out similarly as previously described. This has the same advantages of the freeze thaw platelet lysate autologous culture medium.

FIGS. 2a through 2d show cultured swine MSCs 18 days after culture with three autologous mediums invented here. Swine mesenchymal stromal stem cells taken from the bone marrow and cultured for 18 days in (FIG. 2a) 10% fetal calf serum, (FIG. 2b) 10% autologous serum, (FIG. 2c) 5% platelet rich plasma where platelets were lysed with a freeze thaw cycle, and (FIG. 2d) 5% platelet rich plasma where platelets were lysed with a thrombin activation. They show very similar characteristic to classic MSC morphology.

FIG. 3a through 3d show human mesenchymal stromal stem cells taken from the bone marrow and cultured for 11 or 13 days in (FIG. 3a) 10% fetal calf serum, (FIG. 3b) 10% autologous serum, (FIG. 3c) 5% platelet rich plasma where platelets were lysed with a freeze thaw cycle, and (FIG. 3d) 5% platelet rich plasma where platelets were lysed with a thrombin activation. They show very similar characteristic re MSC morphology. All cultures remained viable and non-contaminated until the end (4 weeks of culture). Cellularity was good with fetal calf serum and platelet rich plasma with freeze thaw but less optimal with autologous serum or thrombin activation.

FIG. 4 shows the flow cytometry CD Profiles in Human Cultured Autologous Bone Marrow Mononuclear Cells in Fetal Calf Serum (FC), Autologous Serum (AS), Freeze and Thaw Platelet Activated Plasma, (F&T PRP) and Thrombin Activated Platelet Activated Plasma (tPRP). Profile of cells from the 4 different culture conditions showed a similar phenotype: CD105+, 73+, 90+, 34−/45−−. This experiment on all patients had essentially identical results. The only anomalies are shown in gray in the first patient run. The Row denoted "expected in" shows expected percentage, and on what type of cells the CD is known to be expressed. The five columns with a * are the 5 CDs sufficient to prove that the cells are a form of MSCs.

For therapeutic purposes the cells are then frozen, shipped to the interventional lab and delivered to the patient. For cardiac applications the preferred deliver is transendocardial intramyocardial delivery or surgical direct injection into the target zone. For gastroesophogeal reflux the cells are delivered through a catheter or transesophogeal ultrasound probe having a penetrating needle element into the region of weakening at the stomach-esophagus junction. For Crohn's disease they are delivered via the rectum through a gastrointestinal catheter designed to navigate in this anatomy with a similar penetrating element and distal steerable member.

The cell compositions and suitable delivery catheters can be provided in a combination cell and device therapeutic. A disposable single use catheter having a distal penetrating needle tip for insertion into target tissues, with the distal penetrating element in fluid communication with a fluid port on the proximal end of said catheter may be used for delivery. Using such a catheter, the cell composition is injected interstitially into the tissue. The cells are delivered at a concentration of between 20M and 40M cells per cc at a dosage of between 20M and 200M cells total. The catheter and a reservoir of cells may be packaged at a manufacturing site and shipped as an assembly to a medical facility for immediate use.

These and other autologous therapeutic cells all have diagnostic value as well. Because these cells are autologous they hold information about the therapeutic potential of the cell and also about the characteristics of the patient that the cultured cells will be administered to that may reflect their responsiveness to therapy. Central to molecular diagnostics is the tissue that is assayed for biomarkers. Throughout this disclosure, the preferred embodiment of tissue for analysis is blood as it is readily available in all patients at all times, and it carries within it the cells of the immune system which recognize known and as yet unknown diseases. Blood is occasionally the source for cell based therapies, and is in intimate communication with other sources from which cell based therapies may be developed and derived: the bone marrow, the adipose tissue, the heart tissue, the nervous system tissues, the skin, the pancreas, etc. However in this specification, it will be recognized that the cells that are the specific source of the cell therapy will have even greater potential to be characterized for their potency in addition to the patient responsiveness to such a therapy due to genetic makeup.

In addition to the mesenchymal stem cells described here, all autologous cell therapy preparations may benefit from this diagnostic strategy. This includes the autologous bone marrow derived cells and cell populations in development at Aldagen and Aastrom Biosciences, as well as the CD34+ cells derived from blood in development at Baxter Healthcare, the autologous cells derived from Adipose tissue in development by Cytori Therapeutics, and other similar cell based therapeutics. Being able to characterize cells for potency by measuring their gene expression provides a means to avoid expensive and risky interventions for those who are less likely to respond. It also provides a means to optimize and enhance this therapeutic strategy over time. For example, if patients without expression of RNAs that code for angiogenic cytokines is noted, these patients may then be selected to receive a modified therapy that includes an angiogenic cytokine—such as described in the trial described by Losordo in which cells are transfected to express VEGF prior to delivery (ClinicalTrials.gov Identifier: NCT00279539).

Example 1

In a first blood draw before tissue is harvested for therapeutic purposes, the gene expression or proteomic patterns in the circulating blood leukocytes are used to determine whether (and to what extent) the patient will respond to various potential cell therapy preparations. In this setting there are options for the preparation of tissue for analysis including: PreAnalytix Pax Gene tubes which are commercially available to stabilize whole blood RNA, isolation of the leukocytes using gravity centrifugation methods and then preserving these with either a PaxGene tube or freezing these cells on dry ice and ultimately at −80 C, or taking fractions of the blood using flow cytometry to remove subsets of cells using antibody probes for surface markers of interest which may be more relevant to the therapeutic strategy in question and ultimately provide for a greater signal to noise ratio when looking at differences between patients as the noise of other cell types will not be present. Further, the blood sample may include the serum and even the RBCs which may be used in proteomic and other analysis using various cytokine protein microarrays and mass spectrometry methodologies.

In its most likely first embodiment the gene expression or proteomic assay will enable a physician to determine whether or not a patient is likely to be responsive to their cells for the clinical indication selected. The gene expression or proteomic patterns may indicate that (1) a simple autologous bone marrow mononuclear cell (ABM MNC) preparation, (2) a preparation of autologous bone marrow mesenchymal cells, (3) an unmodified adipose-derived stromal cell population, or (4) an adipose-derived autologous serum expansion of mesenchymal cells is best suited to treat the patient. This has not been performed previously. The gene expression or proteomic patterns can be detected with assays such as pre-existing assays whole genome microarrays provided by Agilent or Affymetrix and then identifying high fold change genes and using bio-informatic techniques to build classifiers which enables a smaller set of genes to be assayed using PCR or other high resolution measurement approach on a smaller set of genes (.about.20 or so). The methods for analyzing gene expression data included principal components analysis, linear discriminant analysis (LDA, StatSoft, Inc.), logistic regression (SAS Institute, Inc.), prediction analysis of microarrays (PAM) voting, classification and regression trees (TreeNet, Salford Systems), Random Forests, nearest shrunken centroids and k-nearest neighbors.

Once a small set of genes is selected confirming its potential remains nontrivial. Some groups (Deng et al American Journal of Transplantation 2006; 6: 150-160) have used these techniques to develop a linear discriminant analysis system which is relatively simple, other approaches are also possible which do not reduce the output to a simple scalar score. One approach involves ranking the genes for their ability to independently separate the groups and constructing a map that considers the independent score of each gene coupled with the relative score based on all more significant genes. Each gene creates three scenarios: A probability greater than 50+X % that patient is a responder, B probability greater than 50+X % that patient is a non-responder, or AB indeterminant in which neither A nor B is true. X may be selected and need not be that large for this technique to work well. The first gene then defines three classes: A1, B1, and AB1. The second gene builds on this scoring and one gets nine separate classifications possible: A1A2, A1B2, A1AB2, B1A2, B1B2, B1AB2, AB1A2, AB1B2, AB1AB2. A third gene similarly results in 81 independent states that may be assessed and so on. Such a graphical readout is possible for tens of genes which with color coding of the As and Bs one can begin to readily interpret patterns where there is high confidence on therapeutic effectiveness without discarding important data that may be useful for future analysis and interpreted graphically for up to 20 ranked genes (including quality control genes such as plant genes). If X is selected to be vanishingly small, a binary score is possible that makes tracking the decision aspects of each gene contributor to the algorithm much simpler.

As yet undefined algorithms may be employed in this invention as there is significant ongoing work in this area.

The tissue source for therapeutic cells can also be used for diagnostic purposes. In the preferred embodiment autologous bone marrow mononuclear cells (MNCs) are obtained in a small aspirate and sent to the laboratory to assess (1) potency of ABM as a therapeutic for a clinical indication, (2) the relative potency of the mesenchymal stromal cells that would be cultured from these cells, and (3) the ease and or likelihood that MSCs may be successfully cultured from the MNCs.

All autologous cell preparations may benefit from this strategy. Further these techniques may be applied to a wide host of clinical situations such as Graft Versus Host disease, Crohn's disease and other autoimmune diseases, periodontal repair, orthopaedic repair, and the like.

(4) Determining Susceptibility to Treatment

The following describes a method to determine, roughly, the susceptibility of patient populations to the autologous cell therapy. This description could address many different diseases such as heart failure, acute myocardial infarction, chronic ischemia, cardiovascular disease, peripheral vascular disease, or other cardiovascular disease as well as Crohn's disease and other autoimmune diseases, periodontal repair, and orthopaedic repair. For clarity we shall focus on heart failure. To accomplish this, small populations of patients suffering from heart failure are tested both for a wide array of gene expressions and for response to cell therapy. These small populations of patients are tested for a large number of gene expression signatures, markers etc., which may be detected with whole genome assays and interrogating numerous variables in the genome analysis. These patients are also treated with suitably promising autologous cell therapies, such as ACMEAMs (autologous serum expanded autologous mesenchymal cells), where the cells are injected into diseased cardiac tissue of the patient. After this therapeutic injection, patients are tested for typical indications of cardiac health, such as cardiac output, ejection fraction, ventricular wall motion, exercise tolerance, quality of life and the like (including many advanced invasive and non-invasive measurements).

Patients are then divided into groups, essentially those that are responsive to the treatment and those that are not. Each group is tested with a whole genome assay, which is interrogated under many variables in genomic analysis. The genomic assays of the two groups are compared, to ascertain differences in gene expressions that are consistent between the two groups. From the comparison of the gene expressions fold changes found in the responsive population to those found in the non-responsive population, candidate genes which are expressing differentially between the two groups. The goal is to develop a set of up to 20 genes that may be measured from the same autologous tissue (preferably from the source material of the therapeutic cells) indicative of a responder, but to identify a pattern of gene expressions that are indicative of a responder. Numerous genes may express identically in both populations, but several genes will express differentially. Those genes may be ignored, and need not be assayed, so that the assay consists of test for those genes which express differentially between responding and non-responding groups. Thus, the gene expression/proteomic signature profile to determine responders, or to determine non-responders, is developed with a small group of patients. Such an assay is best validated on a second independent population in a subsequent clinical trial.

Genes of particular interest might include genes listed SEQ ID NO: 1 through SEQ ID NO: 8832 of U.S. Pub. 20070037144 incorporated herein by reference.

After determining the group of gene expressions that indicate responsiveness (or that indicate non-responsiveness) to a particular cell therapy for a particular cardiac or cardiovascular condition, assays may be manufactured using RT-PCR or other similar technologies to detect the gene expressions indicative of responsiveness, or non-responsiveness, to one or more potential cell therapies. Prospective patients are then tested with the assays to determine if they are likely to be responsive, or non-responsive, to a particular cell therapy. This is accomplished by testing the cells obtained from the patient, subjecting the cells to the assay, and determining from the assay if the patient is likely to be a responder or a non-responder. It is likely that in some cases, no information will be available from the assay to inform the effectiveness of therapy.

For those identified as probably non-responsive, cell therapy may be avoided as a likely ineffective treatment, or initiated with a clear understanding that it is unlikely to be effective. This would save significant expense. For those identified as likely responders, the therapy may be accomplished by drawing blood in several blood draws, separating the serum from the blood to provide an autologous culture medium for that particular patient, aspirating a volume of bone marrow from the patient, and expanding mesenchymal stem cells derived from the bone marrow in autologous culture medium.

The cell therapy may be targeted on the basis of a single gene expression if it is clear that the single gene expression is an effective indicator of a patient's likely responsiveness to the autologous cell therapy. In this case, the method may be implemented by providing a diagnostic kit to determine whether a patient will respond to an autologous cell therapy for treatment of cardiovascular disease which includes a system for detecting gene expression comprising a single isolated DNA molecule which detects expression of a gene, a sample of autologous tissue the bone marrow, blood, or adipose tissue of the patient from which the putative therapeutic is derived and whose gene expression levels are to be measured. Cell therapy may be targeted on the basis of many variable gene expressions, without determination of a single controlling gene expression, by providing a prognostic kit to determine whether a patient will respond to an autologous cell therapy for treatment of cardiovascular disease, which includes a system for detecting gene expression comprising at least two, and perhaps dozens of isolated DNA molecules wherein each isolated DNA molecule detects expression of a gene. In each instance, the gene expression detected by the assay is analyzed and compared to the expression of control groups to determine the susceptibility of the particular patient to the cell therapy. One simple example may be identification of risk factors related to poor angiogenic potency by assessing the cells upon aspiration.

By developing a diagnostic step that involves information on the therapeutic being delivered in the therapeutic process, additional information on the therapy, its responders, and its non-responders will be developed over time. Although the initial value is binary decision of whether a patient will respond or not because of (i) their genetic makeup and (ii) the characteristics of the therapeutic autologous cells will have power over time other details may also emerge regarding best dosage, best subpopulations of cells, whether or not one or more strategies to enhance a particular genes expression levels would improve therapy and the like.

The two value propositions to autologous cell therapies such as those described here is that they are safe and that they contain information specific to the therapeutic and the patient. These value propositions are believed to be enhanced the closer to truly autologous a putative therapeutic strategy is.

While the preferred embodiments of the devices, diagnostic kits, and methods have been described in reference to the environment in which they were developed, they are merely illustrative of the principles of the inventions. For example, the gene expression signature for a disease such as heart failure could be developed based on surrogate in vitro and in vivo animal assays for potency and subsequently validated and refined in clinical study. Systemic correlation of in vitro and small animal in vivo surrogate potency assays of MCS to gene expression profiles of the harvested source tissue as well as cultured cells from this tissue can be performed. Potential mechanisms of action of MSCs could be assessed through four potency assays. The anti-apoptotic potential of the cells will be assayed by co-culture with rat myocytes, Hoescht staining of the later and expression of Bcl2/Bax by western blotting. Growth factors secretion, by RT-PCR on SDF-1, HGF, IGF and VEGF will be measured as they are seen as responsible for the pro-angiogenic potential of the MSCs. Cells will also be differentiated in cardiomyocytes using 5 azacytidine as transdifferentiation has also been described as a putative mechanism of action. Further surrogate identifiers of potency for preclinical development of a gene signature includes: the colony-forming capacity of BM-MNCs, response of cells to stromal cell-derived factor 1 (SDF-1), response to vascular endothelial growth factor (VEGF), and in vivo neovascularization capacity as measured by laser Doppler-derived relative limb blood flow in mice treated with BM-MNCs.

The methods described above provide for development of a population of autologous stem cells for treatment of disease, by injection of expanded stem cells into tissue of the patient in or near areas affected by the disease. Development of the population of stems cells is, as described above, accomplished by harvesting blood and its components from the patient, in two or more times separated by a week, and creating a culture medium that is entirely autologous, having no animal serum or allogenic culture additives, but instead being augmented with autologous serum or autologous plasma (activated as described above), and expanding the autologous stem cells in that culture medium.

Other embodiments and configurations may be devised without departing from the spirit of the inventions and the scope of the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10035982B2). An electronic copy of the "Sequence Listing" will also be available from the USPTO upon request and payment of the fee set forth in 37 CFR 1.19(b)(3).

What is claimed is:

1. A method of treating a patient having a disease selected from the set of heart failure, myocardial ischemia, myocardial infarction, peripheral vascular disease, and an autoimmune disease, said method comprising injecting an expanded population of mesenchymal stem cells into the tissue of the patient in or near the target area of the disease thereby ameliorating an effect of the disease, said therapeutic cell population having been expanded in autologous medium as follows:

harvesting blood from a donor in two visits separated between one and three weeks;

harvesting bone marrow cells from the donor;

forming a culture medium from said blood that contains no animal serum and comprises 10% autologous serum obtained from the donor; and expanding a population of mesenchymal stem cells from the bone marrow cells in the culture medium.

2. The method of claim 1 where the injecting comprises penetrating a tip of a needle into the tissue and introducing the expanded population of mesenchymal stem cells into the tissue through the needle.

3. The method of claim 1, wherein the population of mesenchymal stem cells is phenotypically characterized by the presence of the following surface markers: CD105, CD73 and CD90.

4. The method of claim 1, wherein the population of mesenchymal stem cells is phenotypically characterized by the absence of the following surface markers: CD34 and CD45.

5. The method of claim 1, wherein the population of mesenchymal stem cells is phenotypically characterized by the presence of the following surface markers: CD105, 73 and CD90, and the absence of CD34 and CD45.

6. The method of claim 1, wherein the expanded mesenchymal stem cells are injected interstitially into target areas through a disposable single use catheter having a distal penetrating needle tip for insertion into target areas in fluid communication with a fluid port on the proximal end of said catheter and in which the expanded mesenchymal stem cells are delivered at a concentration of between 20M and 40M cells per cc at a dosage of between 20M and 200M cells total.

7. The method of any one of claim 1 wherein the expanded mesenchymal stem cells are injected interstitially into the target areas through a catheter.

* * * * *